United States Patent
Stubbs et al.

(10) Patent No.: US 8,538,550 B2
(45) Date of Patent: Sep. 17, 2013

(54) IMPLANTABLE DEVICE FAILSAFE MODE FOR MRI

(75) Inventors: Scott R. Stubbs, Maple Grove, MN (US); Joseph M. Bocek, Seattle, WA (US); Hiten J. Doshi, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 275 days.

(21) Appl. No.: 12/976,876

(22) Filed: Dec. 22, 2010

(65) Prior Publication Data

US 2011/0160786 A1 Jun. 30, 2011

Related U.S. Application Data

(60) Provisional application No. 61/290,776, filed on Dec. 29, 2009.

(51) Int. Cl.
*A61N 1/00* (2006.01)

(52) U.S. Cl.
USPC ............ 607/63; 607/4; 607/31; 607/60

(58) Field of Classification Search
USPC .................................. 607/4, 31, 60, 63
See application file for complete search history.

(56) References Cited

U.S. PATENT DOCUMENTS

| 6,678,560 | B1 | 1/2004 | Gilkerson et al. |
| 7,363,080 | B2 | 4/2008 | Stubbs et al. |
| 7,373,200 | B2 | 5/2008 | Stubbs et al. |
| 7,483,744 | B2 | 1/2009 | Stubbs et al. |
| 7,509,167 | B2 | 3/2009 | Stessman |
| 2007/0150010 | A1 | 6/2007 | Stubbs et al. |
| 2007/0239231 | A1* | 10/2007 | Ginggen ............... 607/63 |
| 2009/0138058 | A1 | 5/2009 | Cooke et al. |
| 2009/0157127 | A1* | 6/2009 | Sowder et al. ............. 607/4 |
| 2009/0157146 | A1 | 6/2009 | Linder et al. |

* cited by examiner

*Primary Examiner* — Nicole F Lavert
(74) *Attorney, Agent, or Firm* — Schwegman Lundberg & Woessner, P.A.

(57) ABSTRACT

An implantable device, such as a pacer, defibrillator, or other cardiac rhythm management device, can include a failsafe backup, such as a separate and independent safety core that can assume control over operation of the implantable device from a primary controller. In an example, the safety core can include a normal first safety core operating mode and a magnetic resonance imaging (MRI) second safety core operating mode that can provide different functionality from the normal first safety core operating mode.

20 Claims, 6 Drawing Sheets

IMPLANTABLE DEVICE FAILSAFE MODE FOR MRI

CLAIM OF PRIORITY

This application claims the benefit of priority under 35 U.S.C. §119(e) of U.S. Provisional Patent Application Ser. No. 61/290,776, entitled "IMPLANTABLE DEVICE FAILSAFE MODE FOR MRI", filed on Dec. 29, 2009, which is herein incorporated by reference in its entirety.

BACKGROUND

Implantable medical devices (IMDs) can perform a variety of diagnostic or therapeutic functions. For example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), or cardiac resynchronization therapy (CRT) devices, among others. Nuclear magnetic resonance imaging (MRI), is a medical imaging technique that can be used to visualize internal structure of the body. MRI is an increasingly common diagnostic tool, but can pose risks to a person with an IMD, such as a patient undergoing an MRI scan or a person nearby MRI equipment, or to people having a conductive implant.

In a MR field, an item, such as an IMD, can be referred to as "MR Safe" if the item poses no known hazard in all MRI environments. In an example, MR Safe items can include non-conducting, non-metallic, non-magnetic items, such as a glass, porcelain, a non-conductive polymer, etc. An item can be referred to as "MR Conditional" in the MR field if the item has been demonstrated to pose no known hazards in a specified MRI environment with specified conditions of use (e.g., static magnetic field strength, spatial gradient, time-varying magnetic fields, RF fields, etc.). In certain examples, MR Conditional items can be labeled with testing results sufficient to characterize item behavior in a specified MRI environment. Testing can include, among other things, magnetically induced displacement or torque, heating, induced current or voltage, or one or more other factors. An item known to pose hazards in all MRI environments, such as a ferromagnetic scissors, can be referred to as "MR Unsafe."

OVERVIEW

An implantable device, such as a pacer, defibrillator, or other cardiac rhythm management device, can include a failsafe backup, such as a separate and independent safety core that can assume control over operation of the implantable device from a primary controller. In an example, the safety core can include a normal first safety core operating mode and a magnetic resonance imaging (MRI) second safety core operating mode that can provide different functionality from the normal first safety core operating mode.

Example 1 can include subject matter comprising or using an implantable medical device, comprising: a primary controller circuit; a safety core circuit, separate from the primary controller circuit, the safety core circuit configured to operate independently from the primary controller circuit; a safety core operating mode storage circuit, coupled to the safety core circuit, the safety core operating mode storage circuit configured to store safety core operating mode information to control whether the safety core circuit is configured to operate in a normal first safety core operating mode or to operate in a magnetic resonance imaging (MRI) second safety core operating mode that is associated with different functionality than the first safety core operating mode; and a reset controller circuit, coupled to the primary controller circuit and the safety core circuit, the reset controller circuit configured to transition control of operating the implantable medical device from the primary controller circuit to the safety core circuit when a fault or error condition is detected.

In Example 2, the subject matter of Example 1 can optionally comprise an MRI detector circuit, coupled to the safety core operating mode storage circuit, and wherein the safety core operating mode storage circuit is configured to select the safety core operating mode in response to whether the MRI detector circuit detects that an MRI apparatus is or could be present or in use nearby the implantable medical device.

In Example 3, the subject matter of any one of Examples 1-2 can optionally be configured such that the normal first safety core operating mode includes heart contraction sensing turned on or enabled and the MRI second safety core operating mode includes heart contraction sensing turned off or disabled.

In Example 4, the subject matter of any one of Examples 1-3 can optionally be configured such that the normal first safety core operating mode includes anti-tachyarrhythmia shock therapy turned on or enabled and the MRI second safety core operating mode includes anti-tachyarrhythmia shock therapy turned off or disabled.

In Example 5, the subject matter of any one of Examples 1-4 can optionally be configured such that the normal first safety core operating mode is configured to provide unipolar pacing and the MRI second safety core operating mode is configured to provide bipolar pacing.

In Example 6, the subject matter of any one of Examples 1-5 can optionally be configured such that the normal first safety core operating mode is configured to provide bi-ventricular pacing and the MRI second safety core operating mode is configured to provide single-ventricle pacing.

In Example 7, the subject matter of any one of Examples 1-6 can optionally be configured such that the normal first safety core operating mode is configured to provide intrinsic heart contraction sensing and to provide pacing in a mode that inhibits a pace when an intrinsic heart contraction is sensed, and wherein the MRI second safety core operating mode is configured with intrinsic heart contraction sensing turned off or disabled and is configured to provide pacing in an asynchronous mode that paces without regard to whether an intrinsic heart contraction is present.

In Example 8, the subject matter of any one of Examples 1-7 can optionally be configured such that the normal first safety core operating mode is configured to provide bi-ventricular pacing and the MRI second safety core operating mode is configured to provide single-ventricle pacing.

In Example 9, the subject matter of any one of Examples 1-8 can optionally be configured such that the normal first safety core operating mode is configured to provide intrinsic heart contraction sensing and to provide pacing in a mode that inhibits a pace when an intrinsic heart contraction is sensed, and wherein the MRI second safety core operating mode is configured with intrinsic heart contraction sensing turned off or disabled and is configured to provide pacing in an asynchronous mode that paces without regard to whether an intrinsic heart contraction is present.

In Example 10, the subject matter of any one of Examples 1-9 can optionally comprise a primary controller operating mode storage circuit, coupled to the primary controller circuit, the primary controller operating mode storage circuit configured to store primary controller operating mode information to control whether the primary controller circuit is configured to operate in a normal first primary controller operating mode or to operate in a magnetic resonance imaging (MRI) second primary controller operating mode that is associated with different functionality than the first primary controller operating mode, wherein the safety core operating mode storage circuit is configured to return the safety core operating mode to the normal first safety core operating mode when the primary controller operating mode storage circuit returns the primary controller operating mode to the normal first primary controller operating mode.

Example 11 can include, or can optionally be combined with the subject matter of any one of Examples 1-10 to include: operating an implantable medical device under control of a primary controller circuit to provide a diagnostic or therapy to a subject; detecting a fault or error condition in the implantable medical device; and in response to the detected fault or error condition, automatically transitioning operation of the implantable medical device from control by the primary controller circuit to control by a separate back-up circuit including a normal first operating mode and an MRI second operating mode that is associated with different functionality than the first operating mode.

In Example 12, the subject matter of any one of Examples 1-11 can optionally comprise detecting that an MRI device is indicated to be present near the implantable medical device; in response to detecting that the MRI device is indicated to be present, operating the implantable medical device under control of the back-up circuit in the MRI second operating mode.

In Example 13, the subject matter of any one of Examples 1-12 can optionally be configured such that detecting that an MRI device is indicated to be present comprises detecting electromagnetic energy associated with the MRI device.

In Example 14, the subject matter of any one of Examples 1-13 can optionally be configured such that detecting that an MRI device is indicated to be present comprises detecting a user-programmed indication that is associated with an MRI procedure to be performed on the patient.

In Example 15, the subject matter of any one of Examples 1-14 can optionally be configured such that the normal first operating mode includes heart contraction sensing turned on or enabled and the MRI second operating mode includes heart contraction sensing turned off or disabled.

In Example 16, the subject matter of any one of Examples 1-15 can optionally be configured such that the normal first operating mode includes anti-tachyarrhythmia shock therapy turned on or enabled and the MRI second operating mode includes anti-tachyarrhythmia shock therapy turned off or disabled.

In Example 17, the subject matter of any one of Examples 1-16 can optionally be configured such that the normal first operating mode is configured to provide unipolar pacing and the MRI second operating mode is configured to provide bipolar pacing.

In Example 18, the subject matter of any one of Examples 1-17 can optionally be configured such that the normal first operating mode is configured to provide bi-ventricular pacing and the MRI second operating mode is configured to provide single-ventricle pacing.

In Example 19, the subject matter of any one of Examples 1-18 can optionally be configured such that the normal first operating mode is configured to provide intrinsic heart contraction sensing and to provide pacing in a mode that inhibits a pace when an intrinsic heart contraction is sensed, and wherein the MRI second operating mode is configured with intrinsic heart contraction sensing turned off or disabled and is configured to provide pacing in an asynchronous mode that paces without regard to whether an intrinsic heart contraction is present.

In Example 20, the subject matter of any one of Examples 1-19 can optionally comprise returning the safety core operating mode to the normal first operating mode upon returning a primary controller operating mode from a MRI second primary controller operating mode to a normal first primary controller operating mode.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

1. MRI Overview

Figure 1:
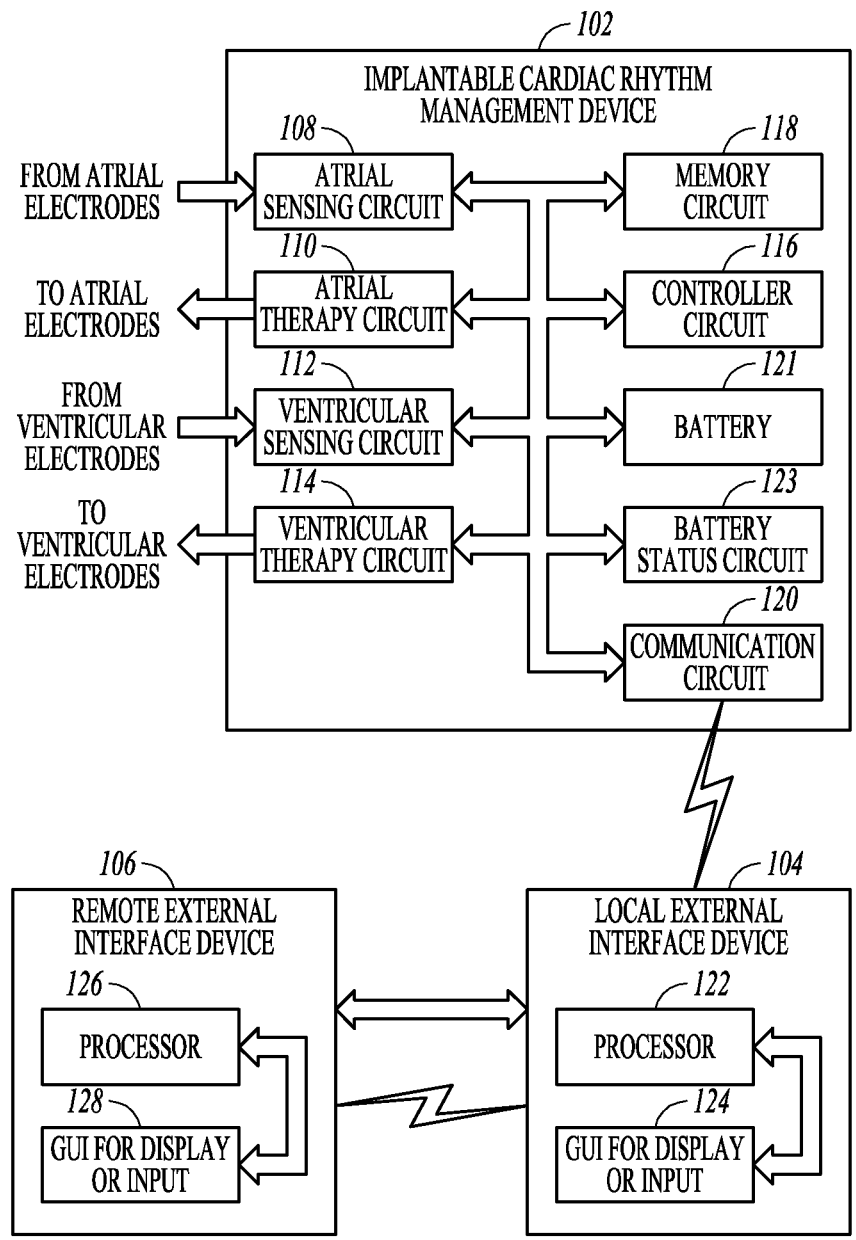
FIG. 1 illustrates an example of portions of a cardiac function management system and an environment in which it is used.

Nuclear magnetic resonance (NMR) devices (e.g., an MRI scanner, an NMR spectrometer, or other NMR device) can produce both static and time-varying magnetic fields. For example, an MRI scanner can provide a strong static magnetic field, $B_0$, such as to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered such as to alter the alignment of specified nuclei (e.g., within a particular volume or plane to be imaged within the subject). The power, phase, and range of frequencies of the one or more RF excitation pulses can be selected, such as depending on the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during MR, such as to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization" of signals detected by the RF receiver, such as by using frequency discrimination. Using a gradient field allows a volume or plane to be imaged more efficiently. In a gradient field example, signals received from relaxing nuclei can include energy in respective unique frequency ranges corresponding to the respective locations of the nuclei.

Active MRI equipment can induce unwanted torques, forces, or heating in an IMD or other conductive implant, or can interfere with operation of the IMD. In certain examples, the interference can include disruption in sensing by the IMD, interference in communication between the IMD and other implants or external modules during MRI operation, or disruption in monitoring or therapeutic function of the IMD.

During an MRI scan, the one or more RF excitation pulses can include energy delivered at frequencies from less than 10 MHz to more than 100 MHz, such as corresponding to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, such as including individual time-varying gradient fields provided in each of the axes to provide imaging in multiple dimensions.

In an example, the static field, $B_0$, can induce unwanted forces or torques on ferromagnetic materials, such as steel or nickel. The forces or torques can occur even when the materials are not directly within the "bore" of the MRI equipment—because significant fields can exist near the MRI equipment. Moreover, if an electric current is switched on or off in the presence of the $B_0$ field, a significant torque or force can be suddenly imposed in the plane of the circulation of the current, even though the $B_0$ field itself is static. The induced force or torque can be minimal for small currents, but the torque can be significant for larger currents, such as those delivered during defibrillation shock therapy. For example, assuming the circulating current is circulating in a plane normal (e.g., perpendicular) to the static field, the torque can be proportional to the magnitude of the $B_0$ field, multiplied by the surface area of the current loop, multiplied by the current.

Time-varying fields, such as the gradient field or the field associated with the RF excitation pulse, can present different risks than the static field, $B_0$. For example, the behavior of a wire loop in the presence of a time-varying magnetic field can be described using Faraday's law, which can be represented by $$\varepsilon = -\frac{d\Phi_{B_1}}{dt},$$

in which $\varepsilon$ can represent the electromotive force (e.g., in volts), such as developed by a time-varying magnetic flux. The magnetic flux can be represented as $$\Phi_{B1} = \iint_S B_1 \cdot dS,$$

in which $B_1$ can represent an instantaneous magnetic flux density vector (e.g., in Webers per square meter, or Tesla). If $B_1$ is relatively uniform over the surface S, then the magnetic flux can be approximately $\Phi_{B1} = |B_1||A|$, where A can represent the area of the surface S. Operating MRI equipment can produce a time-varying gradient field having a slew rates in excess of 100 Tesla per second (T/s). The slew rate can be similar to a "slope" of the gradient field, and is thus similar to $$\frac{d\Phi_{B_1}}{dt}.$$

The electromotive force (EMF) of Faraday's law can cause an unwanted heating effect in a conductor—regardless of whether the conductor is ferromagnetic. EMF can induce current flow in a conductor (e.g., a housing of an IMD, one or more other conductive regions within an IMD, or one or more other conductive implants). The induced current can dissipate energy and can oppose the direction of the change of the externally applied field (e.g., given by Lenz's law). The induced current tends to curl away from its initial direction, forming an "eddy current" over the surface of the conductor, such as due to Lorentz forces acting upon electrons moving through the conductor. Because non-ideal conductors have a finite resistivity, the flow of induced current through the conductor can dissipate heat. The induced heat can cause a significant temperature rise in or near the conductor over the duration of the scan. The power dissipated by the eddy current can be proportional to the square of both the peak flux density and the frequency of the excitation.

Generally, induced currents, such as induced by the RF magnetic excitation pulse, can concentrate near the surface of a conductor, a phenomenon that can be referred to as the skin effect. The skin effect can limit both the magnitude and depth of the induced current, thus reducing power dissipation. However, the gradient field can include energy at a much lower frequency than the RF magnetic excitation field, which can more easily penetrate through the housing of the IMD. Unlike the field from the RF excitation pulse, the gradient field can more easily induce bulk eddy currents in one or more conductors within the IMD housing, such as within one or more circuits, capacitors, batteries, or other conductors.

Aside from heating, the EMF can create, among other things, non-physiologic voltages that can cause erroneous sensing of cardiac electrical activity, or the EMF can create a voltage sufficient to depolarize cardiac tissue or render the cardiac tissue refractory, possibly affecting pacing therapy. In an illustrative example, an IMD can be connected to one or more leads, such as one or more subcutaneous or intravascular leads positioned to monitor the patient, or to provide one or more therapies to the patient. In this illustrative example, a surface area of a "circuit" including the lead, the housing of the IMD, and a path through at least partially conductive body tissue between an electrode on the lead and the IMD housing can be more than 300 square centimeters, or more than 0.03 square meters. Thus, using Faraday's law, the electromotive force (EMF) developed through the body tissue between the electrode (e.g., a distal tip or ring electrode) of the lead and the housing of the IMD can be more than 0.03 square meters times 100 t/s, or more than 3 volts.

2. Fault Fail-Safe (Safety Core) Overview

An implantable cardiac rhythm management device can include a microprocessor or microcontroller based device. Its normal operation can be disrupted by fault events. A fault event can either arise from a hardware failure or a software problem. The disruption in normal operation, if left unchecked, could cause the device to behave in way that may be problematic for the patient. An IMD can include fault detection circuitry which, upon detecting a fault condition, can cause the IMD to enter a state that is believed to be safe for the patient. In an example, a watchdog timer can be provided. A watchdog timer can include a hardware timer that runs continuously. The watchdog timer can be recurrently reset by the main control software of the IMD during normal operation. If a fault disrupts such normal operation of the main control software (e.g., a software crash), however, such that the watchdog timer is allowed to time out, this can generate a reset signal that can re-initialize the system, or that can cause the device to revert to specified operating state. In one approach, reset and recovery mechanism in a low-power IMD can be an ad hoc design, which can attempt to provide a limited recovery mechanism, such as in response to a specific fault condition. Such a mechanism can be complex to get to work correctly, and it may not effectively respond to unanticipated fault conditions.

In contrast to an approach that employs an ad hoc fault recovery mechanism, another approach, such as described with respect to the present systems and methods herein, can help enable an IMD to consistently recover from transient faults. In an example, upon detection of a fault, a reset controller can issue a reset command. In an example, various sub-systems of an IMD can then be reset together, rather than resetting such individual sub-systems independently. This can help provide deterministic behavior. In an example, a primary device controller can be included in the IMD, such as to provide full-capability diagnostics and therapy. In an example, the primary device controller can be interfaced to a reset controller, which can manage the reset process. A fail-safe sub-system, which can be referred to herein as a "safety core," can be included, such as to provide certain limited therapy or other functionality as backup, such as while the reset process proceeds.

Before issuing the reset command, in an example, the reset controller can cause primary device controller operation to halt, can enable a back-up therapy subsystem, or can cause the primary device controller to log the failure condition. However, if the fault interferes with the ability to perform logging, the reset process can be allowed to continue unconditionally. The activation of the back-up therapy subsystem can also occur unconditionally, e.g., independent of the success or failure of the logging process. During the reset process, the primary device controller can execute a complete self-test and re-initialization, such as to ensure that the primary device controller and any ancillary controlled sub-systems are functioning correctly, before control is returned from the back-up safety core. If the self-test fails, the device can remain under control of the back-up safety core.

Illustrative examples of an IMD, such as an implantable cardiac rhythm management device, such as including a primary controller and a fail-safe backup safety core are described in:

Stubbs et al., U.S. Pat. No. 7,363,080, entitled SYSTEM AND METHOD FOR PROVIDING BRADYCARDIA THERAPY BY IMPLANTABLE DEVICE IN PRESENCE OF SYSTEM FAULTS, assigned to Cardiac Pacemakers, Inc., which is incorporated herein by reference in its entirety, including is description of systems and methods using a safety core, such as for providing bradycardia therapy;

Stubbs et al., U.S. Pat. No. 7,373,200, entitled SYSTEM AND METHOD FOR PROVIDING TACH-YARRHYTHMIA THERAPY BY IMPLANTABLE DEVICE IN PRESENCE OF SYSTEM FAULTS, assigned to Cardiac Pacemakers, Inc., which is incorporated herein by reference in its entirety, including its description of systems and methods using a safety core, such as for providing tachyarrhythmia therapy;

Stubbs et al., U.S. Pat. No. 7,483,744, entitled SYSTEM AND METHOD FOR RECOVERING FROM TRANSIENT FAULTS IN AN IMPLANTABLE MEDICAL DEVICE, assigned to Cardiac Pacemakers, Inc., which is incorporated herein by reference in its entirety, including its description of systems and methods using a safety core;

Stubbs et al., U.S. Patent Publication No. US 2007/0150010 A1, entitled CARDIAC PACEMAKER WITH PACING RATE MONITORING, which was filed on Dec. 22, 2005, now issued as U.S. Pat. No. 7,826,897, assigned to Cardiac Pacemakers, Inc., which is incorporated herein by reference in its entirety, including its description of systems and methods configured to operate in multiple rate monitoring zones to inhibit or prevent excessively high-rate pacing during a particular mode of device operation; and Sowder et al., U.S. Patent Publication No. US 2009/0157127 A1, entitled TELEMETRY DURING SAFETY MODE OPERATION, which was filed on Dec. 4, 2008, pending, assigned to Cardiac Pacemakers, Inc., which is incorporated by reference herein in its entirety, including its description of systems and methods such as for allowing communication between an IMD and an external device during safety mode operation.

Also, an illustrative example of a limited functionality safe back-up mode of operation, such as an electrosurgery mode, is described in Gilkerson et al. U.S. Pat. No. 6,678,560 entitled CARDIAC RHYTHM MANAGEMENT SYSTEM WITH ELECTROSURGERY MODE, which is assigned to Cardiac Pacemakers, Inc., and which is incorporated by reference herein in its entirety, including its description of systems and methods for providing limited functionality during a safe back-up mode of operation, such as during electrosurgery.

3. System Overview

FIG. 1 illustrates an example of portions of a cardiac function management system 100 and an environment in which it is used. In certain examples, the system 100 includes an implantable cardiac rhythm or function management device 102, a local external interface device 104, and an optional remote external interface device 106. In certain examples, the implantable device 102 includes an atrial sensing circuit 108, an atrial therapy circuit 110, a ventricular sensing circuit 112, a ventricular therapy circuit 114, a controller circuit 116, a memory circuit 118, a communication circuit 120, a power source such as a battery 121, and a battery status circuit 123.

The atrial sensing circuit 108 is typically coupled to electrodes, such as an intra-atrial electrode or any other electrode that permits sensing of an intrinsic atrial cardiac signal including atrial depolarization information. The atrial therapy circuit 110 is typically similarly coupled to these or other electrodes, such as for delivering pacing, cardiac resynchronization therapy (CRT), cardiac contractility modulation (CCM) therapy, defibrillation cardioversion shocks, or other energy pulses to one or both atria.

The ventricular sensing circuit 112 is typically coupled to electrodes, such as an intra-ventricular electrode or any other electrode that permits sensing of an intrinsic ventricular cardiac signal including ventricular depolarization information. The ventricular therapy circuit 114 is typically similarly coupled to these or other electrodes, such as for delivering pacing, cardiac resynchronization therapy (CRT), cardiac contractility modulation (CCM) therapy, defibrillation/cardioversion shocks, or other energy pulses one or both ventricles.

A controller circuit 116 is coupled to the atrial sensing circuit 108 and the ventricular sensing circuit 112 to receive information from the sensed cardiac signals, and is coupled to the atrial therapy circuit 110 and the ventricular therapy circuit 114 to provide control or triggering signals to trigger timed delivery of the therapy pulses. In an example, the controller circuit 116 can be configured to provide control to help permit the CCM therapy to be effectively delivered, such as in combination with one or more other therapies (e.g., bradycardia pacing, antitachyarrhythmia pacing (ATP), cardiac resynchronization therapy (CRT), atrial or ventricular defibrillation shock therapy) or functionalities (e.g., autothreshold functionality for automatically determining pacing threshold energy, autocapture functionality for automatically adjusting pacing energy to capture the heart, etc.). In an example, this can include providing dedicated modules within the controller circuit 116, or providing executable, interpretable, or otherwise performable code configure the controller circuit 116.

A memory circuit 118 is coupled to the controller circuit 116, such as to store control parameter values, physiological data, or other information. A communication circuit 120 is coupled to the controller circuit 116 to permit radiofrequency (RF) or other wireless communication with an external device, such as the local external interface device 104 or the remote external interface device 106.

In an example, the battery 121 can include one or more batteries to provide power for the implantable device 102. In an example, the battery 121 can be rechargeable, such as by wireless transcutaneous power transmission from an external device to the implantable device 102. The battery status circuit 123 can be communicatively coupled to each of the battery 121 and the controller circuit 116, such as to determine battery status information, for example, indicative of how much energy remains stored in the battery 121. The controller circuit 116 can be configured to alter operation of the implantable device 102, such as based at least in part on the battery status information.

The local external interface device 104 typically includes a processor 122 and a graphic user interface (GUI) 124 or like device for displaying information or receiving user input as well as a communication circuit, such as to permit wired or wireless communication with the remote external interface device 106 over a communications or computer network. Similarly, the remote external interface device 106 typically includes a processor 126 and a graphic user interface (GUI) 128 or like device for displaying information or receiving user input as well as a communication circuit, such as to permit wired or wireless communication with the local external interface device 104 over the communications or computer network. Because the system 100 includes processing capability in the implantable device 102 (e.g., provided by the controller circuit 116), the local external interface device 104 (e.g., provided by the processor 122), and the remote external interface device 106 (e.g., provided by the processor 126), various methods discussed in this document can be implemented at any of such locations, or tasks can be distributed between two or more of such locations.

4. Example of Primary Controller Interaction With Safety Core

Figure 2:
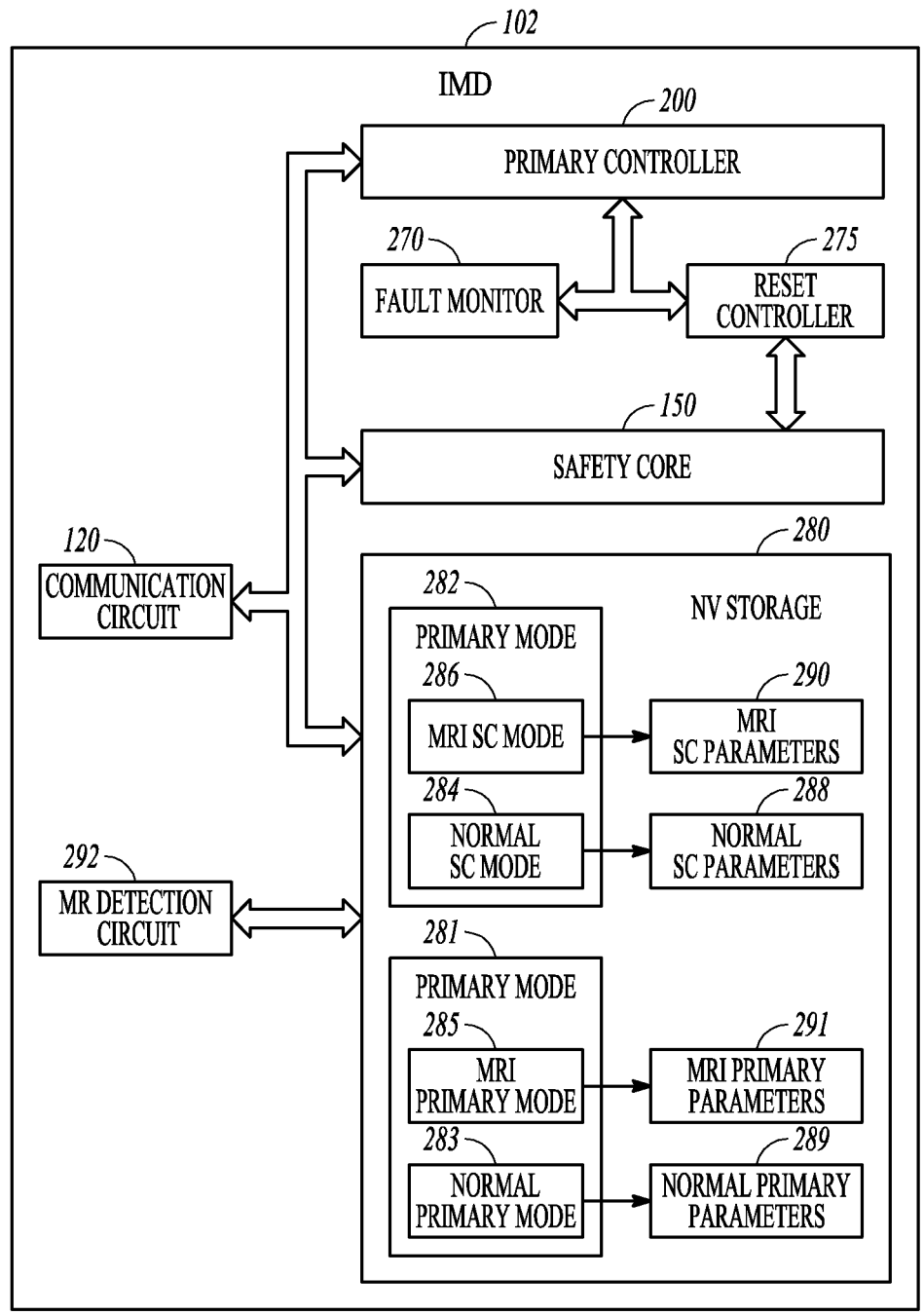
FIG. 2 illustrates an example in which the implantable device can include the controller circuit, which can serve as a primary controller, and can also include a fault monitor circuit, a reset controller, and a back-up safety core.

FIG. 2 illustrates an example in which the implantable device 102 can include the controller circuit 116, which can serve as a primary controller 200, and can also include a fault monitor circuit 270, a reset controller 275, and a safety core 150, such as described in the above-incorporated Stubbs et al., U.S. Pat. No. 7,483,744. In an example, the primary controller 200 can constitute a primary control system of the implantable device 102 device, such as for providing a diagnostic or therapy. The fault monitor 270 can detect one or more kinds of faults. In an example, the fault monitor 270 can include a watchdog timer, a clock deviation monitor, a memory error detection circuit, or other monitor for detecting a faults or an error condition. In an example, the fault monitor 270 or the primary controller 200 can also detect a fault related to the hardware or program execution. When a fault is detected by either the primary controller 200 or the fault monitor 270, a resulting input signifying detection of the fault event can be provided by the fault monitor 270, such as to the reset controller 275. In an example, the reset controller 275 can manage a reset process in response to the detected fault, and can enable the safety core 150 in response to the detected fault, such as for operation of the safety core 150 during the reset process. The safety core 150 can be separate and independent from the primary controller 200, and can include a hardware-based, firmware-based, or similar fail-safe sub-system such as for controlling operation of the implantable device 102, such as for performing relatively limited diagnostic or therapy capability when the primary controller 200 is being reset or is otherwise halted, unavailable, or unreliable, such as due to a system fault.

In an example, the safety core 150 can include a "normal" first safety core operating mode that can provide a first limited set of functionality, such as basic pacing therapy, tachyarrhythmia detection, and shock delivery. In an example, the safety core 150 can provide the first limited set of functionality using hardware-based or firmware-based logic that operates independently from the primary controller 200. In an example, the safety core 150 can additionally or alternatively include an "MRI" second safety core operating mode that can provide a second limited set of functionality that is suitable for use during an MRI scanning procedure or while the implantable device 102 is in close proximity to an MRI scanner, such as described further below. The safety core 150 can provide the second limited set of functionality using hardware-based or firmware-based logic that operates independently from the primary controller 200, in an example.

5. Example of Reset Sequence

Figure 3:
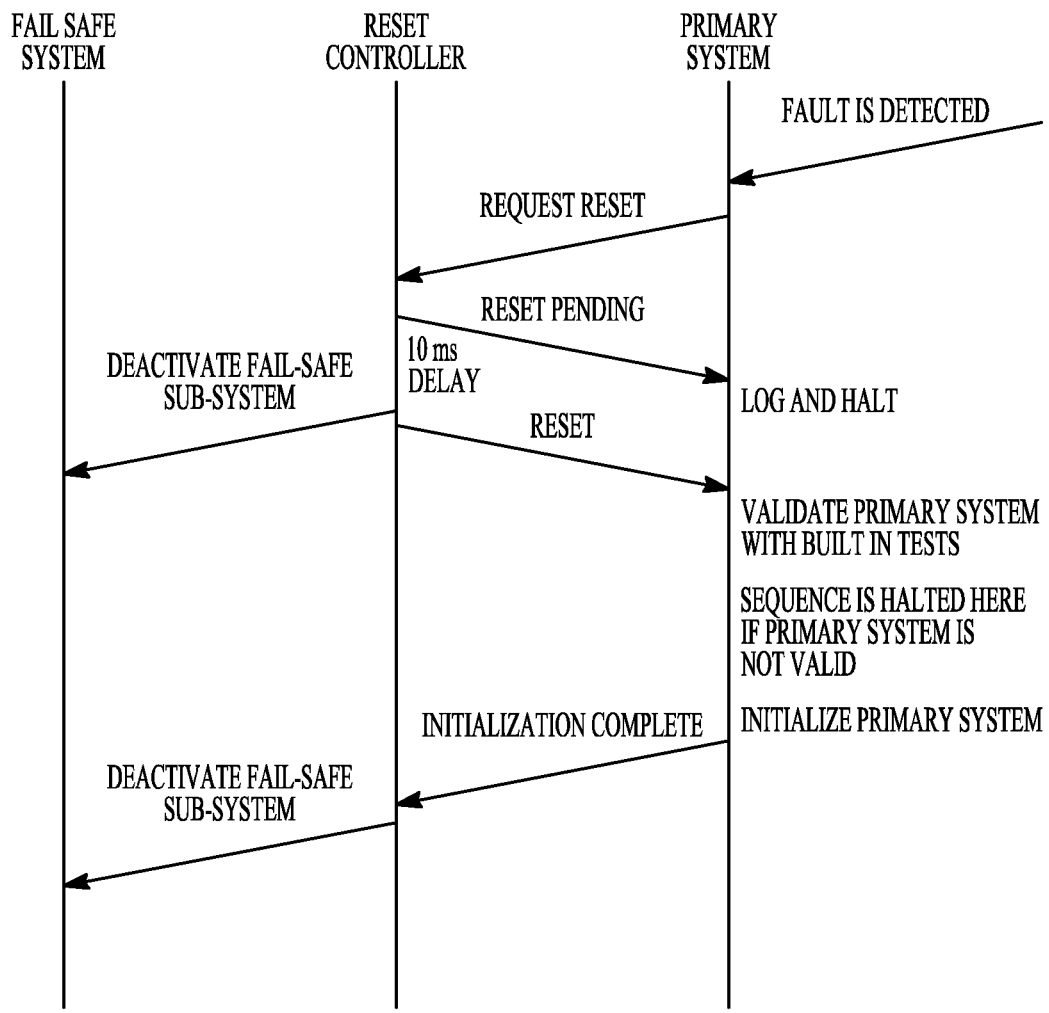
FIG. 3 illustrates an example of a reset sequence.

FIG. 3 illustrates an example of a reset sequence. In an example, the reset sequence can be initiated when the primary controller 200 or the fault monitoring circuitry 270 detects a fault or error condition. In response, information indicating the existence or nature of the fault can be provided to the reset controller 275. In response, the reset controller 275 can raise a pending reset signal. In an example, this pending reset signal can be provided to the primary controller 200, and can initiate logging of the cause of the pending reset by the primary controller 200, such as along with context information for later analysis or reporting. During the pending reset, therapy functions being performed by the primary controller 200 can be halted, such as to inhibit or prevent abnormal therapy behavior. In an example, a delay (e.g., on the order of 10 milliseconds) can ensue, such as to allow the logging operation to complete. This time is arbitrarily specified, and can be adjusted within reason such as to accommodate the logging. In an example, the logging can be performed by the primary controller 200, if possible, but this is not guaranteed as the fault leading to the system reset may be so severe that no further operation of the primary controller 200 is possible. After expiration of the pending reset signal, a reset signal can then be raised by the reset controller 275 and provided to the primary controller 200, such as to initiate one or more built-in self-tests that can be used to validate the primary controller 200. In an example, the fail-safe safety core 150 can be activated by the reset controller 275 so that the implantable device 102 can continue providing service, such as during the logging and during the built-in self test of the primary controller 200. If operation of the primary controller 200 can be validated, the primary controller 200 can be allowed to re-initialize and resume operation. When the initialization process of the primary controller 200 has successfully completed, then the reset controller 275 can deactivate the fail-safe safety core 150.

In an example, the operation of the reset controller 275 can optionally be modified to provide improved tolerance to system faults by including a system-reset monitor, which can detect system resets caused by non-recoverable and persistent faults. The system-reset monitor can provide a mechanism to bound repeated system resets that can occur as a result of faults that are not corrected by system resets. This can help to inhibit or prevent denial of therapy due to non-recoverable or persistent faults. As described above, either software or hardware within the implantable device 102 can generate internal resets, which can be used to reset the primary controller 200 to attempt to recover from a transient fault. In an example, a signal communicated from the local external device 104 to the implantable device 102 can generate a reset of the primary controller 200 in the implantable device 102. This can be referred to as an external reset. In an example, a reset count, such as can be maintained by a counter circuit in the system-reset monitor, can be incremented when an internal reset occurs, and can be cleared by an external reset. In an example, the reset count can be decremented by one count every 48 hours (or other specified time period). The 48 hour time period can start from the first reset and can stop when the reset count is zero. Since many system tests can be executed daily, in an example, this allows faults that occur daily to eventually trip the system-reset monitor. The 48 hour time period can also provide some margin for delay of daily tests. A non-recoverable or persistent fault can be detected when a specified number (e.g., three) of internal resets occur within a 48-hour period. When a non-recoverable or persistent fault is detected, the system-reset monitor can inhibit further attempts to restart the primary controller 200 and can allow the fail-safe backup safety core 150 to continue to maintain limited therapy indefinitely without interruption. In an example, the system-reset monitor can log the three most recent resets, such as in a first-in-first-out (FIFO) buffer. As the reset count is decremented, the oldest logged event can be deleted. An external reset can clear the entire buffer. The logged resets can be interrogated, such as with telemetry. The system-reset monitor can be disabled once it has tripped, such as to inhibit or prevent later internal resets from overwriting data, and can be re-enabled by an external reset.

6. Example of Thread Monitor

Figure 4:
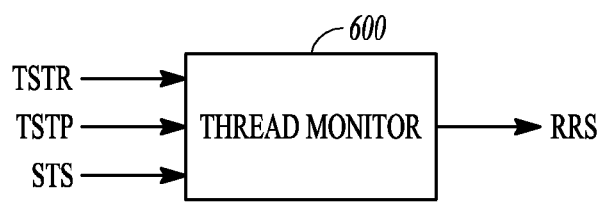
FIG. 4 shows an example of a thread monitor, which can be included in the implantable device, such as for monitoring program behavior in the primary controller.

FIG. 4 shows an example of a thread monitor 600, which can be included in the implantable device 102, such as for monitoring program behavior in the primary controller 200. Such a thread monitor 600 can be used in any implantable medical device that uses software employing separate thread execution techniques. In an example, the thread monitor 600 can detect extended thread execution time or thread sequence anomalies, where a thread can be understood as one of several paths of execution inside a single process or context. A thread can generally be started in response to an event and terminated when the process needs to wait for another event. Threads can execute in either the background or the foreground and can be interrupted.

In one approach, the implantable device 102 can include a watchdog timer circuit, which can include a general purpose timer that can be set to a long enough time interval to inhibit false detections for the longest running threads. In an example, the present system can bound the allowable maximum execution time for every thread. Such bounding can reduce the exposure time of the system to errant operation. Errant behavior of the primary controller 200 can also manifest itself in violations of program execution by failing to abide by one or more established constraints on thread timing or contiguous thread execution (which can be referred to as cross-thread execution). Some devices do not provide detection capabilities for cross-thread operation. The thread monitor 600, such as described herein, can be configured to detect cross-thread operation, such as resulting from single-event upsets (SEUs), process faults, firmware design errors, or one or more other causal events that can result in erroneous program execution.

FIG. 4 illustrates an example of the operation of the thread monitor 600. In an example, each thread can be allocated an identifier ID and a time limit (e.g., in processor cycles), such as at compile time. This information can be used to configure the thread monitor 600, such as at the beginning of the thread execution. When the thread is started by the primary controller 200 software, a thread start signal TSTR, which includes the thread's ID and time limit, can be stored in the thread monitor 600. The thread monitor 600 can be notified that execution of the thread has completed when it receives a thread stop signal TSTP, which can also includes the thread's ID. The thread start and stop signals can usually be managed by the thread scheduling functions of the system software rather than the threads themselves. In an example, a reset request signal RRS can be raised if the thread stop signal is not received before the time limit expires, or if the start and stop IDs are mismatched. In an example, the thread monitor 600 can returns the most recent start ID, stop ID, time limit, and remaining time in response to a status STS signal received from the primary controller 200 software, such as to provide a context to allow thread interruption. The thread monitor 600 can thus provide a way to detect erroneous thread execution in a manner that bounds the thread behavior in terms of time and space. Such fault detection can provides a measure of safety that may not be available with a typical watchdog timer.

7. Example of MRI-Mode Safety Core

As described above, in an example, the safety core 150 can include a "normal" first safety core operating mode and an "MRI" second safety core operating mode, such as described above with respect to FIG. 2, which shows an example of how the controller circuit 116 can serve as a primary controller 200, and a separate and independent safety core 150 can be included to provide back-up for the primary controller 200, such as in the event of a fault or error condition that could jeopardize proper operation of the primary controller 200.

In FIG. 2, the implantable device 102 can include a non-resettable (by a system reset) or nonvolatile (NV) storage circuit 280, such as an electrically programmable and electrically erasable EEPROM nonvolatile storage circuit, or one or more non-resettable registers, or the like. In an example, the NV storage circuit 280 can include a safety core mode storage location 282 that can store information indicating whether the safety core 150 should operate in the normal first safety core operating mode 284 or the MRI second safety core operating mode 286. In an example, this can include a single bit that distinguishes between these two different modes. In an example, this can include information distinguishing between more than two different modes of operating the safety core 150. In an example, the normal first safety core operating mode 284 can include an associated set of one or more normal first safety core operating mode operating parameters 288 such as for controlling how the safety core 150 is to operate during the first safety core operating mode 284. In this example, the normal first safety core operating mode 284 can also include an associated set of one or more MRI second safety core mode operating parameters 290 such as for controlling how the safety core 150 is to operate during the MRI second safety core operating mode 286.

In an example, the NV storage circuit 280 can include a primary controller mode storage location 281 that can store information indicating whether the primary controller 200 should operate in a normal primary controller first operating mode 283 or the MRI second primary controller operating mode 285. In an example, this can include a single bit that distinguishes between these two different modes 281, 283 of operating the primary controller 200. In an example, this can be the same bit that distinguishes between the two different safety core operating modes 284, 286. In an example, this can be a different bit than that which distinguishes between the two different safety core operating modes 284, 286. In an example, the mode 281 can include information distinguishing between more than two different modes of operating the primary controller 200. In an example, the normal first primary controller operating mode 283 can include an associated set of one or more normal first primary controller operating mode operating parameters 289 such as for controlling how the primary controller 200 is to operate during the first primary controller operating mode 283. In this example, the normal first primary controller operating mode 283 can also include an associated set of one or more MRI second primary controller mode operating parameters 291 such as for controlling how the primary controller 200 is to operate during the MRI second primary controller operating mode 285.

In an example, the NV storage circuit 280 can be locally or remotely user-programmed, such as via the communication circuit 120. In this way, the mode 282 can be transitioned from the normal first safety core operating mode 284 to the MRI second safety core operating mode 286, such as when the patient is about to undergo an MRI scanning procedure, and back to the normal first safety core operating mode 284, such as when the patient's MRI scanning procedure has been completed. Similarly, the mode 281 can be transitioned from the normal first primary controller operating mode 283 to the MRI second primary controller operating mode 285, such as when the patient is about to undergo an MRI scanning procedure, and back to the normal first primary controller operating mode 283, such as when the patient's MRI scanning procedure has been completed.

In an example, an MR detector circuit 292 can be included, such as to automatically (e.g., without requiring user-programming) transition the mode 282 from the normal first safety core operating mode 284 to the MRI second safety core operating mode 286 when an MR scanner is detected is detected to be present, and back to the normal first safety core operating mode 284, such as when the MR scanner is no longer detected to be present, when a sufficient time has elapsed since the MR scanner was detected to be present (such that the patient's MRI scanning procedure would be expected to be completed), or both.

In an example, the MR detector circuit 292 can similarly automatically transition the mode 281 from the normal first primary controller operating mode 283 to the MRI second primary controller operating mode 285 when an MR scanner is detected is detected to be present, and back to the normal first primary controller operating mode 283, such as when the MR scanner is no longer detected to be present, when a sufficient time has elapsed since the MR scanner was detected to be present (such that the patient's MRI scanning procedure would be expected to be completed), or both.

In an example, the MR detector circuit 292 can include a reed switch, such as to detect the presence of a magnetic field indicative of an MR scanner performing an MR scanning operation nearby.

In an example, the MR detector circuit 292 can include a Hall-effect sensor, such as to detect the presence of an MR field indicative of an MR scanner performing an MR scanning operation nearby. An example of using a Hall effect sensor in an implantable medical device to sense a magnetic field is described in Linder et al. U.S. Patent Pub. No. 20090157146, entitled IMPLANTABLE MEDICAL DEVICE WITH HALL SENSOR, now isued as U.S. Pat. No. 8,121,678,assigned to Cardiac Pacemakers, Inc., which is incorporated herein by reference in its entirety, including its description of using a Hall-effect sensor to detect a magnetic field, such as that of an MRI scanner. An example of using a Hall-effect sensor in conjunction with an MRI operating mode of an implantable medical device is described in Cooke et al. U.S. Patent Pub. No. 20090138058, entitled MRI OPERATION MODES FOR IMPLANTABLE MEDICAL DEVICES, now issued as U.S. Pat. No. 8,014,867,which is assigned to Cardiac Pacemakers, Inc., which is incorporated herein by reference in its entirety, including its description of using a Hall-effect sensor in conjunction with an MRI operating mode of an implantable medical device.

In an example, the MR detector circuit 292 can additionally or alternatively include an inductor saturation detector, such as to detect the presence of an MR field indicative of an MR scanner performing an MR scanning operation nearby. An example of using inductor saturation to perform MRI detection is described in Stessman, U.S. Pat. No. 7,509,167, entitled MRI DETECTOR FOR AN IMPLANTABLE MEDICAL DEVICE, assigned to Cardiac Pacemakers, Inc., which is incorporated herein by reference in its entirety, including its description of using inductor saturation to perform MRI detection.

In operation, when the safety core 150 is activated by the reset controller 275, such as when the fault monitor 270 or the primary controller 200 detects a fault or error condition, then the safety core 150 is activated in that particular mode 282 (e.g., normal mode 284 or, alternatively, the MRI mode 286) to which the NV storage circuit 280 has been programmed (e.g., by user programming, or by an automatic response to detection of an MR magnetic field by the MR detector 292). When so activated, control of the implantable device 102 transitions from the primary controller 200 to the safety core 150, and the safety core 150 uses the one or more operating parameters corresponding to its programmed mode 286 to operate the safety core 150. Table 1 below illustrates an example of some differences in how the safety core 150 can operate in the "normal" first operating mode as compared to its operation in the "MRI" second operating mode.

TABLE 1

Example of Normal and MRI Mode Safety Core Operation

| Parameter or Function | Normal-Mode Safety Core | MRI-mode Safety core |
|---|---|---|
| Pacing | Bi-Ventricular VVI Pacing | Selectable Between (1) Off and (2) VOO, RV-only |
| Electrode Configuration | Unipolar, Bi-V | Bipolar, RV-only |
| Anti-Tachyarrhythmia Shock Therapy | On | Off |

Table 1 illustrates an example in which, during normal safety core operation, when a fault is detected, the safety core 150 assumes control from the primary controller 200, and the following functionality can be provided:

the pacing that is provided is bi-ventricular (both right ventricular (RV) and left ventricular (LV)) pacing in a VVI pacing mode (which includes active ventricular sensing, and inhibiting delivery of a ventricular pace in response to a sensed ventricular contraction);

the electrode configuration used to provide the pacing is unipolar (e.g., a pacing electrode located at the housing of the implantable device 102 is used in conjunction with an RV pacing electrode and an LV/coronary sinus pacing electrode);

the electrode configuration used to provide the sensing is also unipolar (e.g., a pacing electrode located at the housing of the implantable device 102 is used in conjunction with an RV pacing electrode; and tachyarrhythmia sensing is enabled, using the unipolar sensing configuration, and a tachyarrhythmia can be responded to by delivering an anti-tachyarrhythmia defibrillation shock.

By contrast, during MRI-mode safety core operation, when a fault is detected, the safety core 150 assumes control from the primary controller 200, and the following functionality can be provided:

the pacing the is provided is RV-only asynchronous pacing in VOO mode, with sensing turned off, since the presence of the MRI scanner can generated noise that could interfere with proper sensing function and could cause erroneous inhibition or delivery of pacing therapy if sensing were used to control pacing;

the electrode configuration used to provide the pacing is RV bipolar (e.g., paces are delivered between two electrodes located in the RV), since a unipolar pacing configuration can create a larger "loop area" that is more susceptible to MRI scanner noise; and tachyarrhythmia sensing is disabled, since the presence of the MRI scanner can generated noise that could interfere with proper sensing function and could cause erroneous inhibition or delivery of an anti-tachyarrhythmia defibrillation shock, and since delivery of an anti-tachyarrhythmia defibrillation shock within the bore of an MRI scanner would involve large current flow through the defibrillation leads, which in the presence of the MRI magnet could cause an unintended resulting force on the defibrillation lead.

Figure 5A:
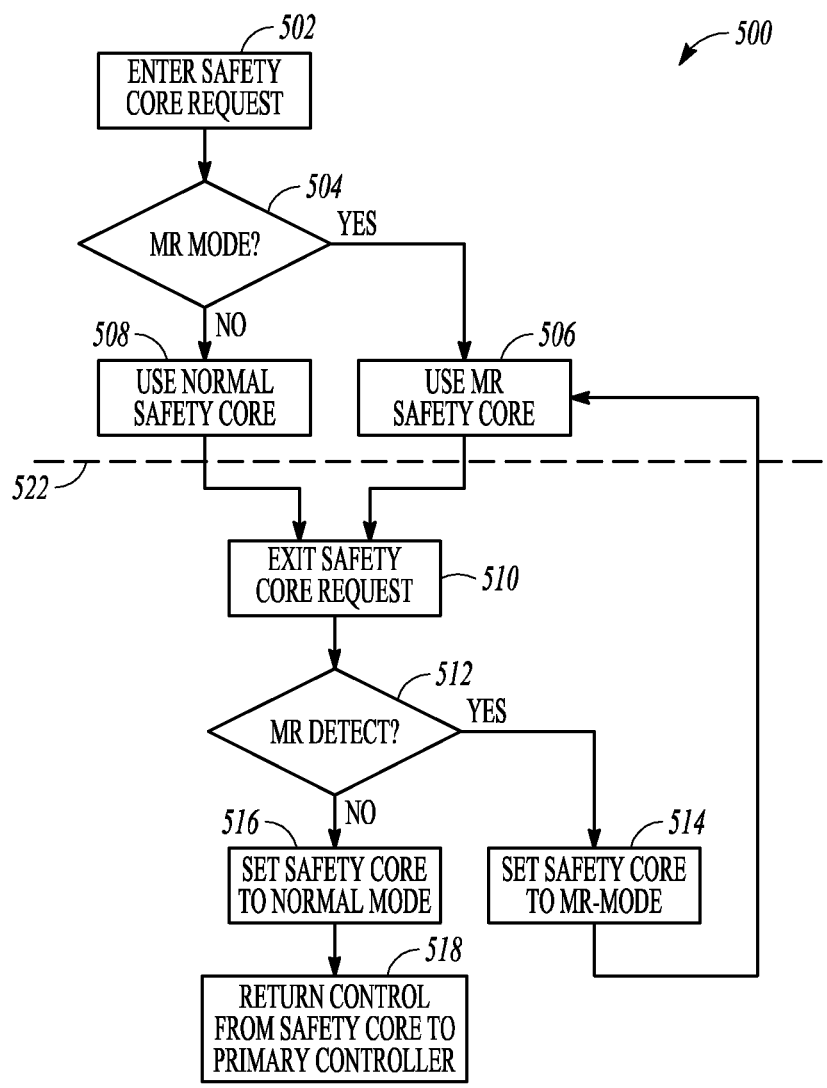
FIG. 5A shows an example of entering and exiting operation under control of the safety core.

FIG. 5A shows an example 500 of entering and (optionally) exiting operation under control of the safety core 150. At 502, a request can be received to transition control from the primary controller 200 to the safety core 150. In an example, this request can be provided by a fault or error condition detected by the fault monitor 270 or the primary controller 200, such as described above. In response, safety core 150 can be activated, such as by the reset controller 275. At 504, it can be determined, such as by the reset controller 275 or the safety core 150, whether the safety core operating mode 282 is the normal first safety core operating mode 284 or the MR second safety core operating mode 286. If in the MR mode 286, then at 506 the safety core 150 can assume control from the primary controller 200 using stored the MRI parameters 290, otherwise, at 508 the safety core 150 can assume control from the primary controller 200 using the stored normal parameters 288.

At 510, an exit safety core request can be received. In an example, the exit safety core request can be generated by a local or remote user communicating such a request via the communication circuit 120. In response, in an example, at 512 it is determined whether an MRI scanner is or could be present. In an example, this can include using the MR detector 292 to determine whether a magnetic field indicative of an MRI scanner is present (such as described above), or checking a timer to determine whether a specified time (e.g., longer than a maximum time associated with an MRI scanning procedure) has elapsed since an MRI scanner was most recently detected, or both. At 512, if it is determined that an MRI scanner is or could be present, then at 514, the safety core operating mode 282 can be set to the MR second safety core operating mode, and operation can return to 506, such that the implantable device 102 can remain under safety core control. This can involve programming the NV storage circuit 280 or programming a mode storage register that is not reset by a system reset, such as described above. At 512, if it is determined that an MRI scanner is not present, then at 516 the safety core operating mode 282 can be set to the normal first safety core operating mode 284, and then at 518 control can be returned from the safety core 150 to the primary controller 200, such as until another enter safety core request is received at 502. Again, setting the safety core operating mode 282 can involve programming the NV storage circuit 280 or programming a mode storage register that is not reset by a system reset, such as described above.

In an example, when a transition from primary controller 200 control of the implantable device 102 to safety core 150 control of the implantable device 102 can be regarded as a non-recoverable event, such that the items 510, 512, 514, 516, and 518 below the dashed line 522 can be omitted. In such an example, the implantable device 102 can continue to remain under control of the safety core 150, such as until explanted.

In an example, the exit safety core request 510 can only be provided by a specified authorized user, such as a field clinical engineer representative of the medical device company providing the implantable device 102. This can involve local or remote communication from the user, such as using the local external interface device 104 or the remote external interface device 106. In an example, the exit safety core request 510 can only be provided by a specified authorized user, such as a physician, such as when the patient is under local observation by the physician such as within a suitable medical facility.

Figure 5B:
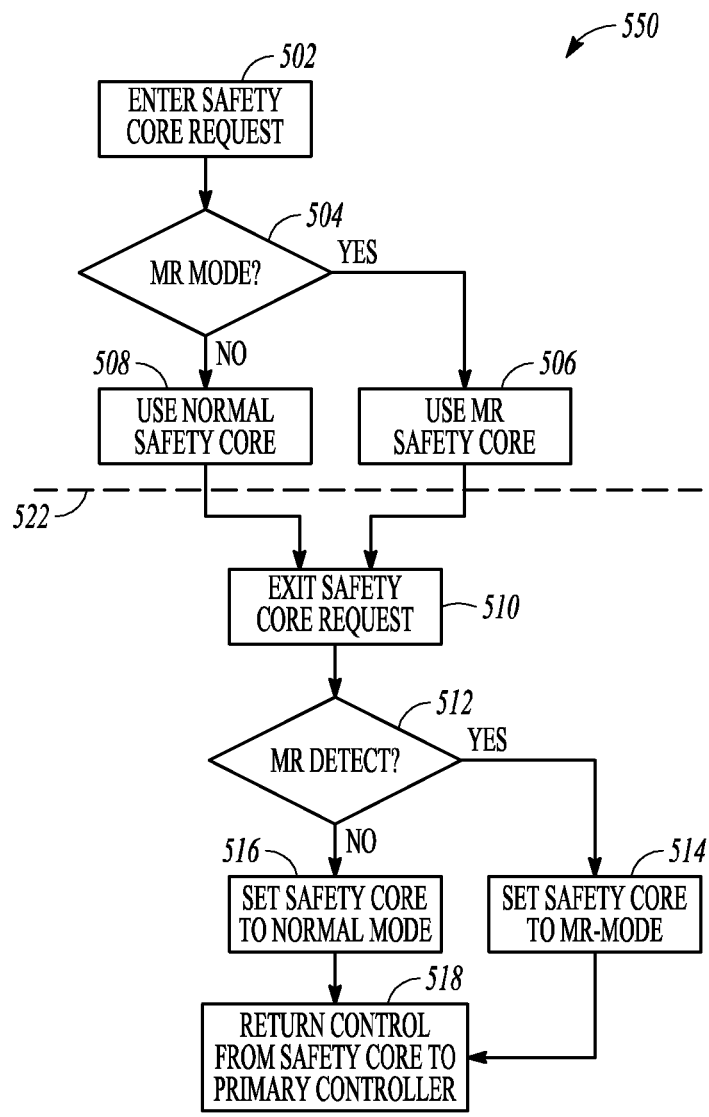
FIG. 5B shows an example of entering and exiting operation under control of the safety core.

FIG. 5B is an example 550 of a method that is similar to that described above with respect to FIG. 5A, except that at 512, if it is determined that an MRI scanner is present, then at 514, the safety core operating mode 282 can be set to the MR second safety core operating mode, but operation is then allowed to continue to 518. In this way, control can be returned from the safety core 150 to the primary controller 200, such as until another enter safety core request is received at 502. Thus, in the example of FIG. 5B, an exit safety core request is permitted to exit the safety core—even in the presence of an MRI scanner, while keeping the safety core operating mode 282 in the MR second safety core operating mode for use in case it is necessary to later re-enter safety core operation, while the example of FIG. 5A, even if an exit safety core request is received (e.g., from a user), it is not permitted to exit from the safety core 150 until the MRI scanner is no longer present.

Figure 6:
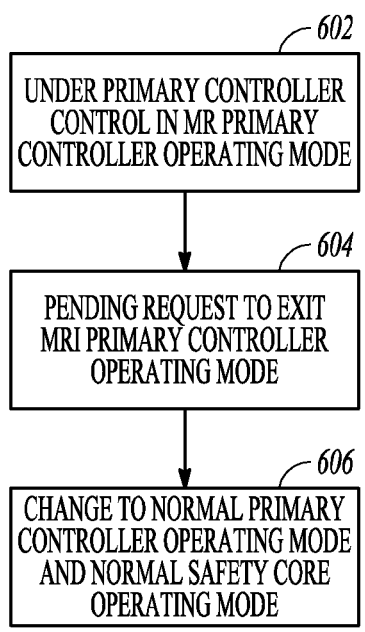
FIG. 6 shows an example of exiting a MRI primary controller operating mode, which can include also exiting an MRI safety core operating mode.

FIG. 6 shows an example of exiting the MRI primary controller operating mode 285 when under control of the primary controller 200, such as when the safety core 150 has not been activated by the reset controller 275. At 602, in an example, the primary controller 200 is in control of operating the implantable device 102, and the implantable device 102 is operating in the MRI primary controller operating mode 285 using the MRI primary parameters 291. This can result, for example, when a user has locally or remotely programmed the implantable device 102 into the MRI primary controller operating mode 285 (e.g., in preparation for the subject carrying the implantable device 102 undergoing an MRI scanning procedure) or when the MR detector circuit 292 has automatically detected the presence of a MR scanner nearby the implantable device 102, such as described above.

At 604, a pending request to exit the MRI primary controller operating mode 285 can be issued, in an example. This can result, for example, when a user locally or remotely programs the implantable device 102 into the normal primary controller operating mode 283 (e.g., when a subject carrying the implantable device 102 has completed the MRI scanning procedure), when a timer circuit has measured that a specified period of time associated with an MRI scanning procedure has elapsed since the MRI primary controller operating mode 285 was entered, when the MR detector circuit 292 detects that an MR scanner is no longer present, or some combination of the above.

At 606, in response to the pending request at 604, the primary controller operating mode 281 is changed from the MRI primary controller operating mode 285 to the normal primary controller operating mode 283, and the safety core operating mode 282 is changed from the MRI safety core operating mode 286 to the normal safety core operating mode 284. In this way, if the reset controller 275 does activate the safety core 150, the safety core 150 will be ready to be activated in the normal safety core operating mode 284, rather than the MRI safety core operating mode 286.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus comprising:
   an implantable medical device, comprising:
   a primary controller circuit;
   a safety core circuit, separate from the primary controller circuit, the safety core circuit configured to operate independently from the primary controller circuit;
   a safety core operating mode storage circuit, coupled to the safety core circuit, the safety core operating mode storage circuit configured to store safety core operating mode information to control whether the safety core circuit is configured to operate in a normal first safety core operating mode or to operate in a magnetic resonance imaging (MRI) second safety core operating mode that is associated with different functionality than the first safety core operating mode; and
   a reset controller circuit, coupled to the primary controller circuit and the safety core circuit, the reset controller circuit configured to transition control of operating the implantable medical device from the primary controller circuit to the safety core circuit when a fault or error condition is detected.

2. The apparatus of claim 1, comprising an MRI detector circuit, coupled to the safety core operating mode storage circuit, and wherein the safety core operating mode storage circuit is configured to select the safety core operating mode in response to whether the MRI detector circuit detects that an MRI apparatus is or could be present or in use nearby the implantable medical device.

3. The apparatus of claim 1, wherein the normal first safety core operating mode includes heart contraction sensing turned on or enabled and the MRI second safety core operating mode includes heart contraction sensing turned off or disabled.

4. The apparatus of claim 3, wherein the normal first safety core operating mode includes anti-tachyarrhythmia shock therapy turned on or enabled and the MRI second safety core operating mode includes anti-tachyarrhythmia shock therapy turned off or disabled.

5. The apparatus of claim 1, wherein the normal first safety core operating mode is configured to provide unipolar pacing and the MRI second safety core operating mode is configured to provide bipolar pacing.

6. The apparatus of claim 5, wherein the normal first safety core operating mode is configured to provide bi-ventricular pacing and the MRI second safety core operating mode is configured to provide single-ventricle pacing.

7. The apparatus of claim 6, wherein the normal first safety core operating mode is configured to provide intrinsic heart contraction sensing and to provide pacing in a mode that inhibits a pace when an intrinsic heart contraction is sensed, and wherein the MRI second safety core operating mode is configured with intrinsic heart contraction sensing turned off or disabled and is configured to provide pacing in an asynchronous mode that paces without regard to whether an intrinsic heart contraction is present.

8. The apparatus of claim 1, wherein the normal first safety core operating mode is configured to provide bi-ventricular pacing and the MRI second safety core operating mode is configured to provide single-ventricle pacing.

9. The apparatus of claim 1, wherein the normal first safety core operating mode is configured to provide intrinsic heart contraction sensing and to provide pacing in a mode that inhibits a pace when an intrinsic heart contraction is sensed, and wherein the MRI second safety core operating mode is configured with intrinsic heart contraction sensing turned off or disabled and is configured to provide pacing in an asynchronous mode that paces without regard to whether an intrinsic heart contraction is present.

10. The apparatus of claim 1, comprising:
    a primary controller operating mode storage circuit, coupled to the primary controller circuit, the primary controller operating mode storage circuit configured to store primary controller operating mode information to control whether the primary controller circuit is configured to operate in a normal first primary controller operating mode or to operate in a magnetic resonance imaging (MRI) second primary controller operating mode that is associated with different functionality than the first primary controller operating mode; and
    wherein the safety core operating mode storage circuit is configured to return the safety core operating mode to the normal first safety core operating mode when the primary controller operating mode storage circuit returns the primary controller operating mode to the normal first primary controller operating mode.

11. A method comprising:
    operating an implantable medical device under control of a primary controller circuit to provide a diagnostic or therapy to a subject;
    detecting a fault or error condition in the implantable medical device; and
    in response to the detected fault or error condition, automatically transitioning operation of the implantable medical device from control by the primary controller circuit to control by a safety core circuit, separate from the primary controller circuit, the safety core circuit configured to operate independently from the primary controller circuit, the safety core circuit configured to include a normal first operating mode and an MRI second operating mode that is associated with different functionality than the first operating mode.

12. The method of claim 11, comprising:
    detecting that an MRI device is indicated to be present near the implantable medical device;
    in response to detecting that the MRI device is indicated to be present, operating the implantable medical device under control of the back-up circuit in the MRI second operating mode.

13. The method of claim 11, wherein detecting that an MRI device is indicated to be present comprises detecting electromagnetic energy associated with the MRI device.

14. The method of claim 11, wherein detecting that an MRI device is indicated to be present comprises detecting a user-programmed indication that is associated with an MRI procedure to be performed on the patient.

15. The method of claim 11, wherein the normal first operating mode includes heart contraction sensing turned on or enabled and the MRI second operating mode includes heart contraction sensing turned off or disabled.

16. The method of claim 15, wherein the normal first operating mode includes anti-tachyarrhythmia shock therapy turned on or enabled and the MRI second operating mode includes anti-tachyarrhythmia shock therapy turned off or disabled.

17. The method of claim 11, wherein the normal first operating mode is configured to provide unipolar pacing and the MRI second operating mode is configured to provide bipolar pacing.

18. The method of claim 11, wherein the normal first operating mode is configured to provide bi-ventricular pacing and the MRI second operating mode is configured to provide single-ventricle pacing.

19. The method of claim 18, wherein the normal first operating mode is configured to provide intrinsic heart contraction sensing and to provide pacing in a mode that inhibits a pace when an intrinsic heart contraction is sensed, and wherein the MRI second operating mode is configured with intrinsic heart contraction sensing turned off or disabled and is configured to provide pacing in an asynchronous mode that paces without regard to whether an intrinsic heart contraction is present.

20. The method of claim 11, comprising returning the safety core operating mode to the normal first operating mode upon returning a primary controller operating mode from a MRI second primary controller operating mode to a normal first primary controller operating mode.

* * * * *